United States Patent
Sakamaki et al.

(10) Patent No.: US 6,579,232 B2
(45) Date of Patent: Jun. 17, 2003

(54) VITAL SIGN MONITOR

(75) Inventors: Takanori Sakamaki, Tokyo (JP); Yasuhiro Fukui, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 0 days.

(21) Appl. No.: 09/815,040

(22) Filed: Mar. 23, 2001

(65) Prior Publication Data

US 2003/0097046 A1 May 22, 2003

(30) Foreign Application Priority Data

May 16, 2000 (JP) .......................................... 2000-143989

(51) Int. Cl.$^7$ ................................................ A61B 5/00
(52) U.S. Cl. ..................................... 600/300; 340/573.1
(58) Field of Search ................................ 600/300, 301; 382/217–223, 128–134; 340/540, 573.1; 607/27; 604/503; 128/200.24, 202.22

(56) References Cited

U.S. PATENT DOCUMENTS

| | | | | |
|---|---|---|---|---|
| 5,320,092 A | * | 6/1994 | Ryder | ..................... 128/202.22 |
| 5,891,178 A | * | 4/1999 | Mann et al. | .................... 607/27 |
| 6,406,426 B1 | * | 6/2002 | Reuss et al. | ................. 600/300 |
| 6,425,395 B1 | * | 7/2002 | Brewer et al. | ......... 128/202.22 |

\* cited by examiner

*Primary Examiner*—Max F. Hindenburg
*Assistant Examiner*—David J. McCrosky
(74) *Attorney, Agent, or Firm*—Sughrue Mion, PLLC

(57) ABSTRACT

The vital signs detected by vital sign detecting means 101 and the data detected by medical apparatus operation detecting means corresponding to each vital sign are sent to judging means 103. The judging means 103 judges the correlation between the vital signs and the medical apparatus operation state, and further judges whether a variation in vital signs detected by the vital sign detecting means 101 is within a range of variation estimated from the medical apparatus operation detected by the medical apparatus operation detecting means 102. And indicating means 104 indicates an alarm or a message on the basis of a judgement result of whether or not the variation in vital signs is within the estimated range of variation.

10 Claims, 8 Drawing Sheets

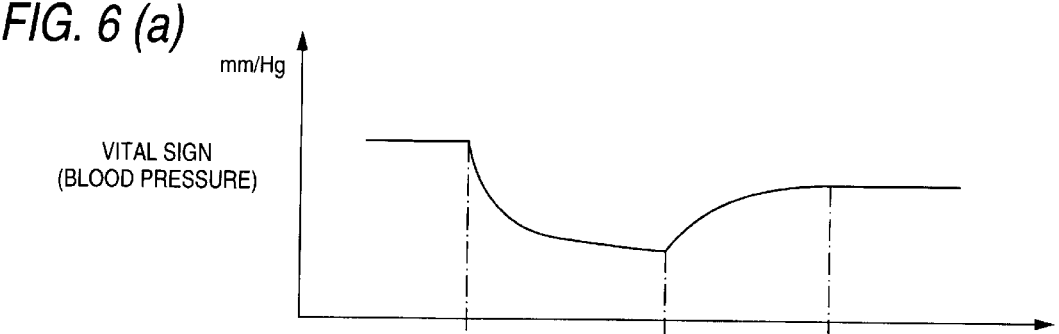
FIG. 6 (a)
FIG. 6 (b)
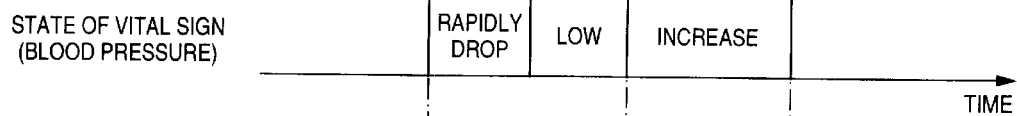
FIG. 6 (c)
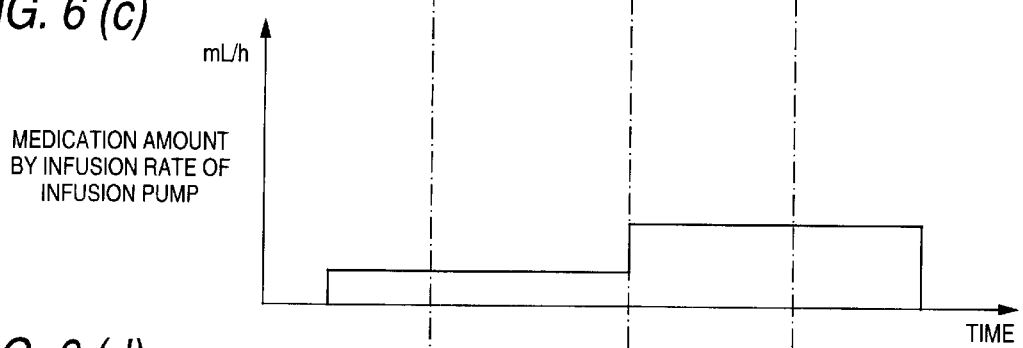
FIG. 6 (d)
FIG. 6 (e)
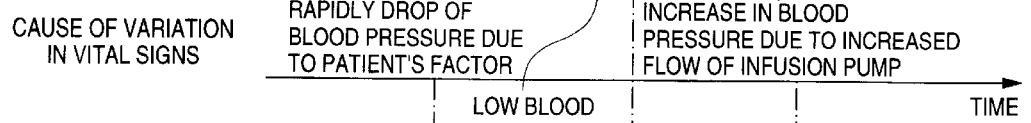
FIG. 6 (f)
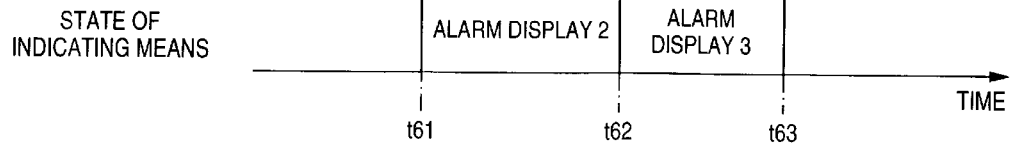

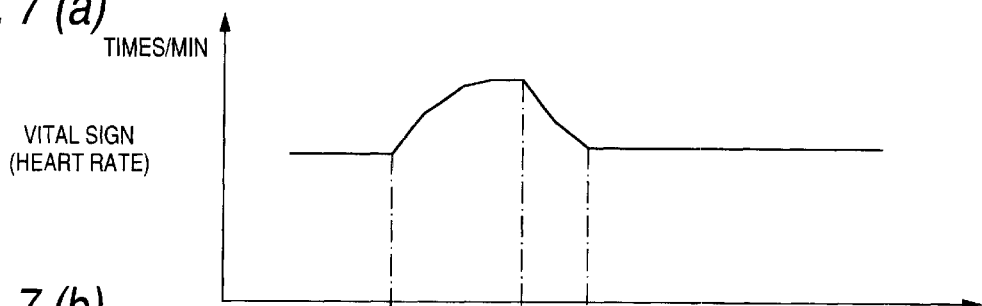
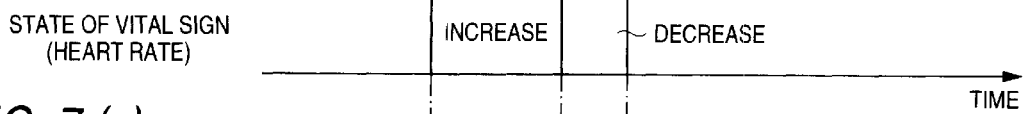
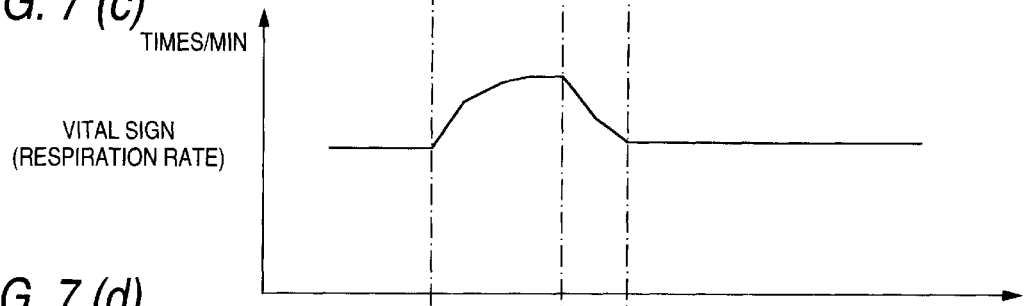
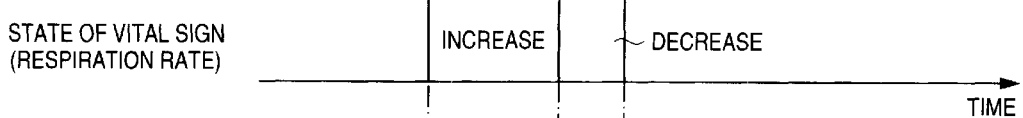
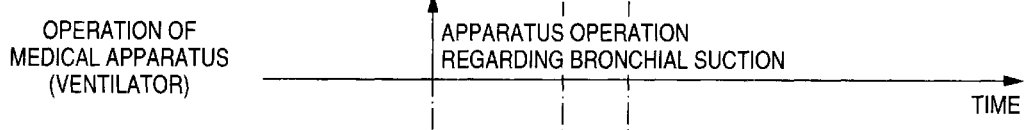
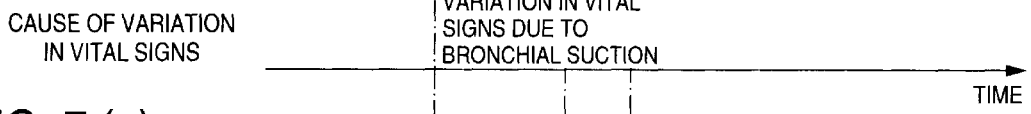
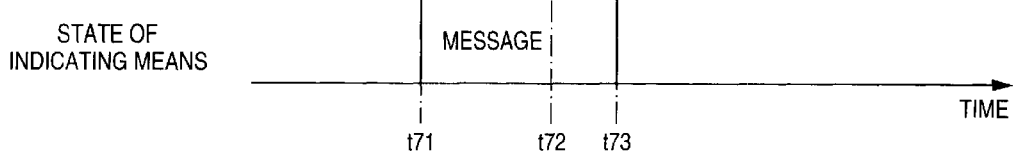

VITAL SIGN MONITOR

BACKGROUND OF INVENTION

1. Field of Invention

The present invention relates to a vital sign monitor achieving a highly reliable alarm function.

2. Related Art

The vital sign monitor is installed at an intensive care unit in the hospital or ward, and informs the clinical staff with an alarm sound at a bedside of the patient, or allows the clinical staff to check by displaying the details on a display monitor, when an abnormal vital sign of the patient is found such as electrocardiograph (heart rate, arrhythmia), blood pressure, respiration, $SpO_2$, body temperature, and urinary volume and so on.

And the clinical staff aware of this alarm sound, hastens to the patient, stops the alarm sound, checks the patient's condition, and gives an appropriate treatment.

In this way, the conventional vital sign monitor mainly pays attention only to a variation in vital signs, without discriminating the cause of the variation in vital signs, and simply recognizes its abnormal condition to indicate an alarm.

Also, the conventional vital sign monitor makes the clinical staff conduct an operation of stopping or suppressing a sound or an indication of the alarm device.

However, the vital sign data measured by the vital sign monitor may contain a great number of artifacts or noises, which are caused by the medical treatment such as the blood sampling or medication performed by the clinical staff, and the patient's related factors such as body movement.

Further, a treatment such as bronchial suction for removing the phlegm within the bronchi, or a pain may become a stimulation to the living body, causing the vital signs to change temporarily, and announcing unnecessary alarm sound in many instances.

In this way, the conventional vital sign monitor does not consider a false alarm due to false recognition of the alarm condition, or a practice situation of the treatment care of the clinical staff, announcing unnecessary alarm in some instances.

Therefore, the alarm function of the vital sign monitor can not obtain the confidence of the clinical staff, and may continue to announce the unnecessary alarm, obstructing the sleeping of other patients. Hence, there are many requests for improvements from the clinical site.

Also, the operation of stopping the alarm sound by the clinical staff is quite different from the operation of the medical apparatus for the treatment. Hence, this operation of stopping the alarm sound may impede the treatment practice of the clinical staff, and further increase the danger of hospital infection by making a touch on such alarm device during the treatment.

SUMMARY OF INVENTION

The present invention has been achieved in the light of the above-mentioned conventional problems and affairs, and it is an object of the invention to provide a vital sign monitor capable of suppressing an unnecessary alarm display by recognizing the cause of a variation in vital signs in consideration of the medical practice of the clinical staff, as well as implementing a highly reliable alarm function by allowing discrimination of the unexpected variation in vital signs.

To accomplish the above-mentioned object, according to a first aspect of the present invention, there is provided a vital sign monitor comprising vital sign detecting means for detecting vital signs, medical apparatus operation detecting means for detecting the operation of a medical apparatus, and judging means for judging the correlation between the vital signs and a medical apparatus operation condition on the basis of the vital signs detected by the vital sign detecting means and the operation condition of the medical apparatus detected by the medical apparatus operation detecting means. Therefore, the cause of a variation in vital signs can be recognized.

According to a second aspect of the present invention, the vital sign monitor is provided by further comprising indicating means for indicating the correlation between the vital signs and the medical apparatus operation condition as an alarm or a message depending upon an instruction signal of the judging means. Therefore, the alarm or message can be indicated in view of the presence or absence of the operation of the medical apparatus.

According to a third aspect of the present invention, there is provided the vital sign monitor including the judging means which judges whether or not a variation in the vital signs detected by the vital sign detecting means is within a range of variation estimated from the operation of the medical apparatus detected by the medical apparatus operation detecting means. Hence, it is possible to make sure of whether or not the variation in vital signs is within the estimated range of variation.

According to a fourth aspect of the present invention, there is provided the vital sign monitor including the indicating means indicates an alarm or a message on the basis of a judgement result of whether or not the variation in the vital signs is within the range of variation estimated. It is possible to make sure of whether or not the variation in vital signs is within the estimated range of variation in terms of an alarm or a message.

According to a fifth aspect of the present invention, there is provided the vital sign monitor including the judging means further judges whether or not the variation in the vital signs detected by the vital sign detecting means is beyond a predetermined range in a state where any change in the operation condition of the medical apparatus is not detected by the medical apparatus operation detecting means, and the indicating means indicates an alarm displaying that the predetermined range is exceeded. Hence, it is possible to make sure of the variation in vital signs irrespective of the operation of the medical apparatus.

According to a sixth aspect of the present invention, there is provided the vital sign monitor such that in the case where the indicating means indicates the alarm in accordance with the correlation when the operation condition of the medical apparatus is detected by the medical apparatus operation detecting means, the judging means instructs the indicating means to indicate an alarm displaying a state of the operation condition of the medical apparatus.

According to a seventh aspect of the present invention, there is provided a vital sign monitor comprising vital sign detecting means for detecting vital signs, clinical staff practice recognizing means for detecting and recognizing a practice of a clinical staff, and judging means for judging the correlation between the vital signs and the practice of the clinical staff on the basis of the vital signs detected by the vital sign detecting means and the practice of the clinical staff recognized by the clinical staff practice recognizing means. Hence, the cause of a variation in vital signs can be recognized.

According to an eighth aspect of the present invention, there is provided the vital sign monitor further comprising indicating means for indicating the correlation between the vital signs and the practice of the clinical staff as an alarm or a message depending upon an instruction signal of the judging means. Hence, the alarm or message can be indicated in consideration of the practice of the clinical staff.

According to a ninth aspect of the present invention, there is provided the vital sign monitor including the judging means judges whether or not a variation in the vital signs detected by the vital sign detecting means is within a range of variation estimated from the practice of the clinical staff recognized by the clinical staff practice recognizing means. Hence, it is possible to make sure of whether or not the variation in vital signs is within the estimated range of variation.

According to a tenth aspect of the present invention, there is provided a vital sign monitor including the indicating means which indicates an alarm or a message on the basis of a judgement result of whether or not the variation in the vital signs is within the estimated range of variation. Hence, it is possible to make sure of whether or not the variation in vital signs is within the estimated range of variation in terms of an alarm or a message.

According to an eleventh aspect of the present invention, there is provided the vital sign monitor including the judging means further judges whether or not a variation in the vital signs detected by the vital sign detecting means is beyond a predetermined range in the state where no change in the practice of the clinical staff is detected by the clinical staff practice recognizing means, and the indicating means indicates an alarm displaying that the predetermined range is exceeded. Hence, it is possible to make sure of the variation in vital signs irrespective of the practice of the clinical staff.

According to a twelfth aspect of the present invention, there is provided the vital sign monitor in the case where the indicating means indicates the alarm in accordance with the correlation when the operation condition of the medical apparatus is detected by the medical apparatus operation detecting means, the judging means instructs the indicating means to indicate an alarm displaying a state of the operation condition of the medical apparatus.

According to a thirteenth aspect of the present invention, there is provided the vital sign monitor including the clinical staff practice recognizing means recognizes the practice of the clinical staff when the medical apparatus is operated.

According to a fourteenth aspect of the present invention, there is provided the vital sign monitor including the clinical staff practice recognizing means recognizes the practice of the clinical staff using image-pickup means.

According to a fifteenth aspect of the present invention, there is provided the vital sign monitor in he case that using the image-pickup means, it is recognized that the clinical staff changes the body position of a patients, or there is body movement of the patient, the indicating means is inhibited to indicate the alarm. Hence, it is possible to suppress unnecessary alarm for the practice of the treatment care by the clinical staff or the body movement of the patient.

BRIEF DESCRIPTION OF DRAWINGS

FIG. 6(a) to (f) are diagrams for explaining an example 2 appearing the effect of the vital sign monitor according to the embodiment of the invention excellently.

FIGS. 7(a) to (g) are diagrams for explaining an example 3 appearing the effect of the vital sign monitor according to the embodiment of the invention excellently.

DETAILED DESCRIPTION OF PREFERRED EMBODIMENTS

The preferred embodiments of the present invention will be described below.

Figure 1:
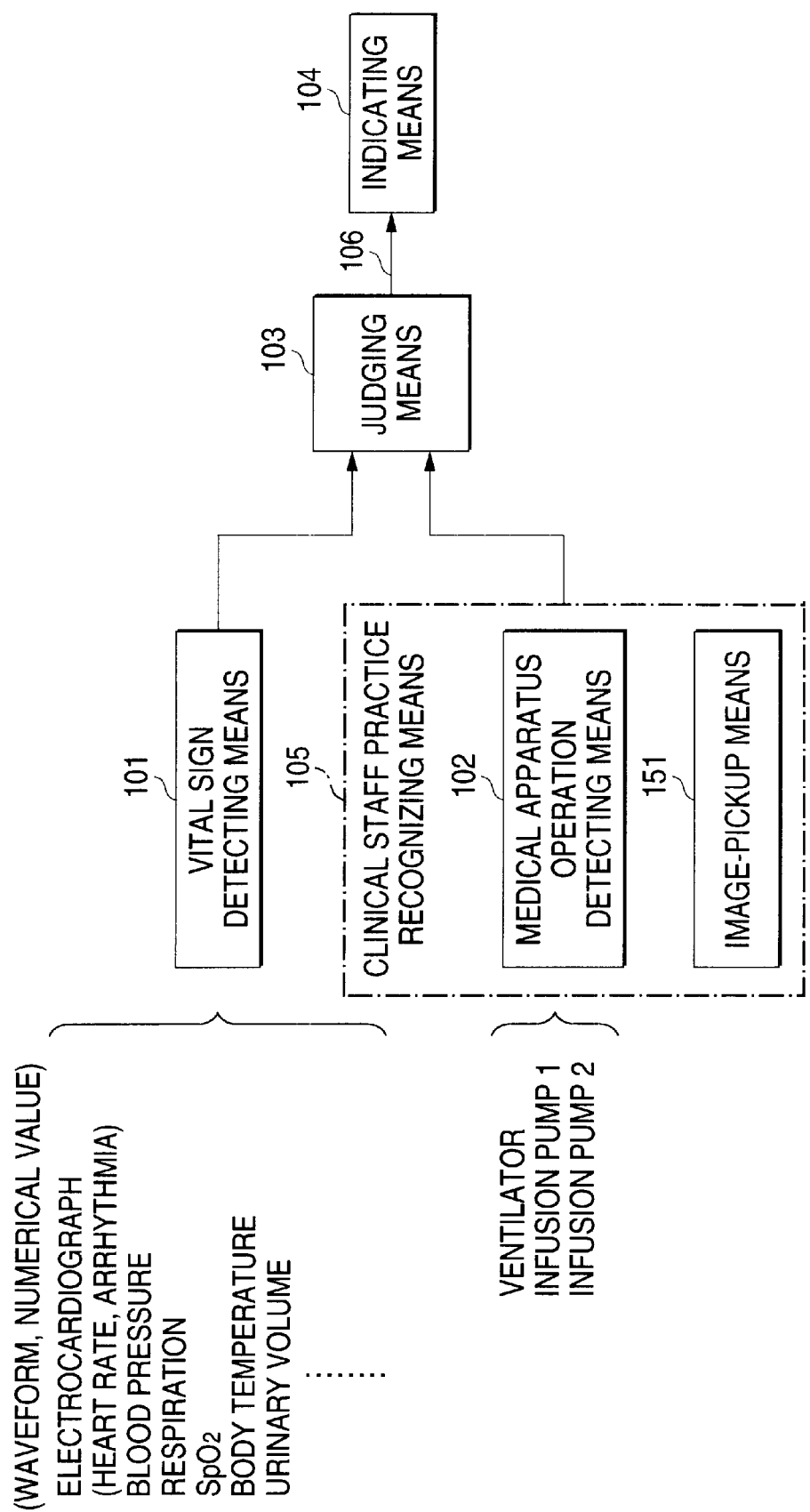
FIG. 1 is a schematic diagram of a vital sign monitor according to an embodiment of the present invention.

FIG. 1 is a schematic diagram of a vital sign monitor according to this embodiment of the invention.

As shown in FIG. 1, the vital sign monitor has vital sign detecting means 101 for detecting vital signs such as electrocardiograph (heart rate, arrhythmia), blood pressure, respiration, $SpO_2$, body temperature, and urinary volume, and the vital signs detected by the vital sign detecting means 101 being transmitted to judging means 103.

The vital sign monitor according to this embodiment also has medical apparatus operation detecting means 102 for a medical apparatus corresponding to the vital signs, such as a ventilator or infusion pumps, for example, the data detected by the means being transmitted to the judging means 103.

The judging means 103 judges the correlation between the vital signs and the medical apparatus operation condition, in which the cause of the variation in vital signs is recognized and the reason is judged.

Further, the judging means 103 judges whether or not the variation in vital signs detected by the vital sign detecting means 101 is within a range of variation estimated from the medical apparatus operation detected by the medical apparatus operation detecting means 102.

An indicating means 104 indicates an alarm or a message based on a result of judging whether or not the variation in vital signs is within the estimated range of variation, when an instruction signal 106 is transmitted from the judging means 103 to the indicating means 104.

Figure 2:
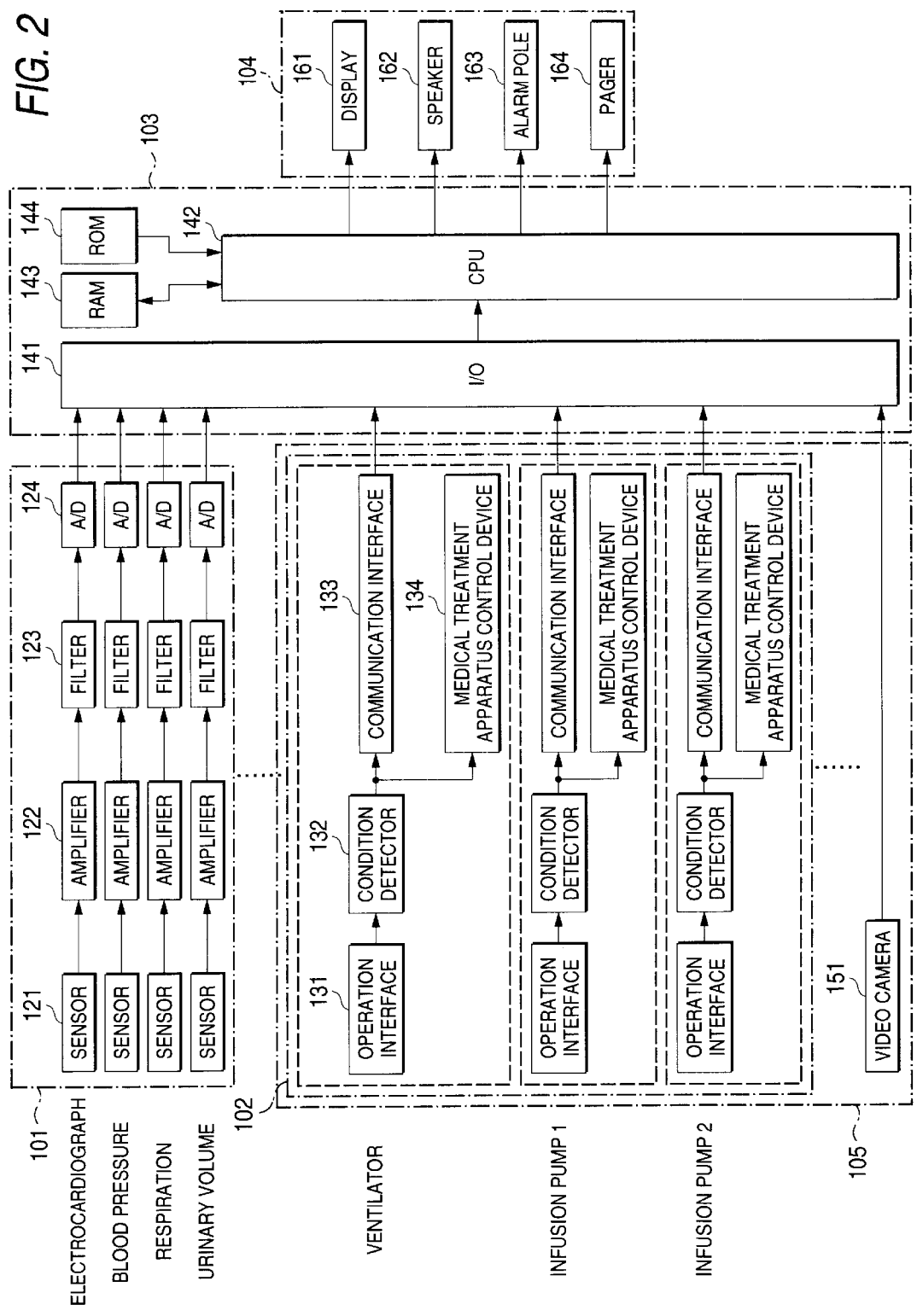
FIG. 2 is a block diagram showing one example of a specific configuration of the vital sign monitor according to the embodiment of the invention.

A specific system configuration of the vital sign monitor according to this embodiment is illustrated in FIG. 2.

In FIG. 2, specifically, the vital sign detecting means 101 for vital signs such as electrocardiograph, blood pressure, respiration and urinary volume is constituted of a sensor 121, an amplifier 122, a filter 123, and an A/D (analog/digital converter) 124.

Also, the medical apparatus operation detecting means 102 for detecting the operation of the medical apparatus is constituted of an operation interface 131, a condition detector 132, a communication interface 133, and a medical treatment apparatus control device 134.

The judging means 103 is constituted of an I/O 141 that is an input section of the data transmitted via the A/D (analog/digital converter) 124 and the communication interface 133, a CPU 142 for controlling the system, a RAM 143 for use in reading or writing the data, and a ROM 144.

The indicating means 104 that is controlled by the judging means 103 is constituted of various types of alarm devices such as a display 161, a speaker 162, an alarm pole 163, and a pager 164.

In this embodiment, the vital sign monitor may have clinical staff practice recognizing means 105 for recognizing the operation of the medical apparatus, or the practice of the clinical staff by the image-pickup means, the detected data being transmitted to the judging means 103.

The clinical staff practice recognizing means 105 can recognize the practice of the clinical staff, owing to the operation of the medical apparatus, employing the medical apparatus operation detecting means 102, and further transmit the information regarding the presence or practice of the clinical staff to the judging means 103 by placing a video camera (image-pickup means) 151 around the patient.

This video camera (image-pickup means) 151 can monitor an event where the clinical staff changes the body position of the patient, or an event where the body movement of the patient is recognized, for example. Upon these events, the judging means 103 provides a control for indicating no alarm while the vital signs fluctuate, if any.

Explanation of Operation

Figure 3:
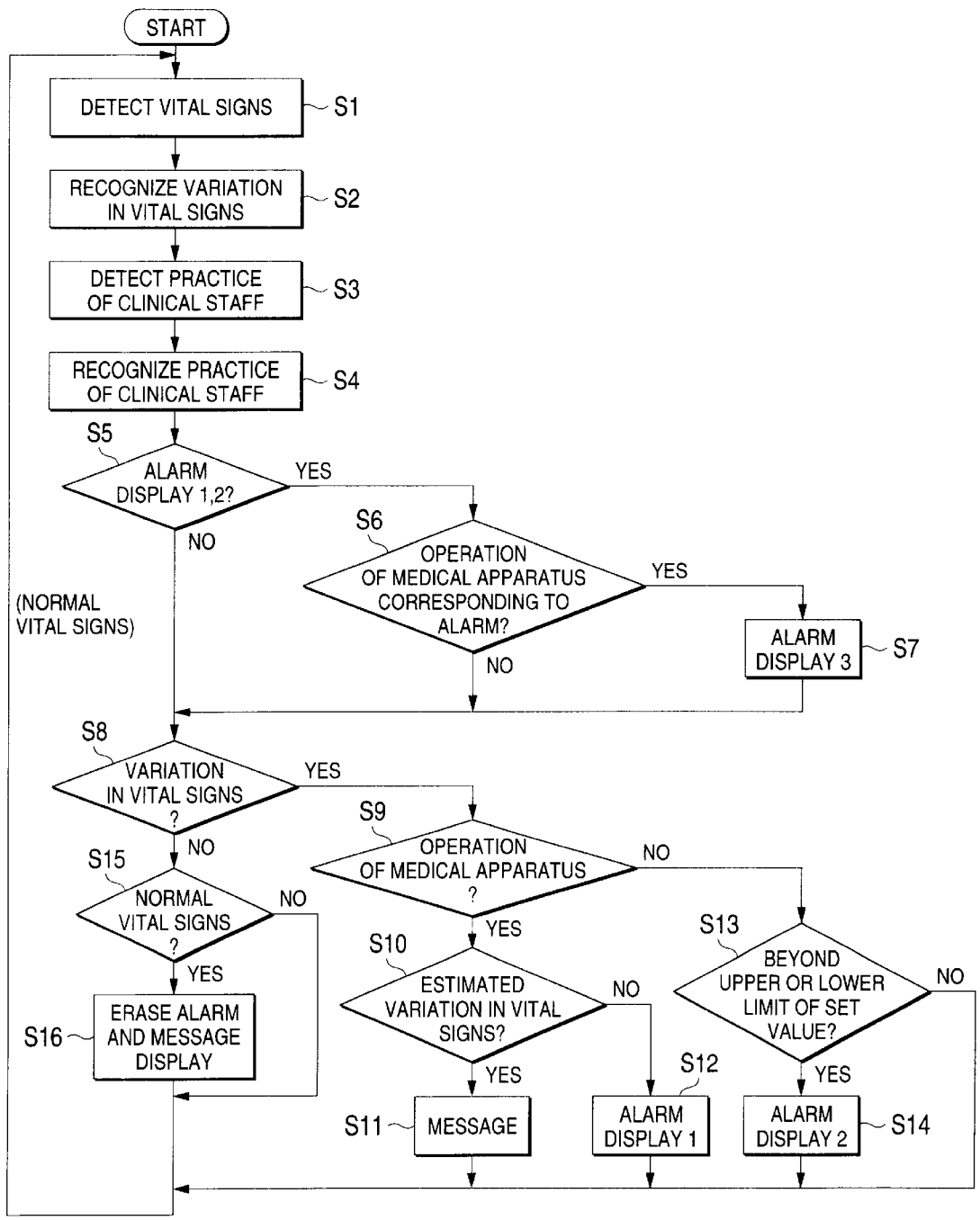
FIG. 3 is a flowchart for explaining the operation of the vital sign monitor according to the embodiment of the invention.

Referring now to a flowchart of FIG. 3, the operation of the vital sign monitor according to this embodiment will be described below in detail.

First of all, at step S1, a vital sign is detected, employing the vital sign detecting means 101. At step S2, a variation in this vital sign is recognized.

At the same time, at step S3, the practice of the clinical staff is detected by the clinical staff practice recognizing means 105. At step S4, the practice of the clinical staff is recognized. In this stage, the clinical staff practice recognizing means 105 is constituted of the medical apparatus operation detecting means 102 for detecting a medical apparatus operation and image-pickup means 151 of course, the clinical staff practice recognizing means 105 is capable of employing one of the medical apparatus operation detecting means 102 and the image-pickup means 151.

At step S5, the judging means 103 judges whether or not alarm display 1 or alarm display 2 has been made. If any alarm display has been made (Y), the judging means 103 further judges at step S6 whether or not the operation of the medical apparatus corresponding to the alarm display is performed. If the operation of the medical apparatus is performed (Y), the indicating means 104 indicates an alarm display 3 at step S7.

At step S8, the judging means 103 judges whether or not there is a variation in vital signs. If there is any variation (Y), the judging means 103 further judges whether or not the operation of the medical apparatus is performed at step S9. If the operation of the medical apparatus is performed at step S9 (Y), the judging means 103 further judges whether or not there is any variation in vital signs at step S10. If the variation in vital signs is in an estimated state (Y), the indicating means 104 indicates a message display at step S11. If the variation in vital signs is out of the estimated state (N) at step S10, the indicating means 104 indicates an alarm display 1 at step S12.

If there is no operation of the medical apparatus (N) at step S9, the judging means 103 judges whether or not the variation in vital signs is beyond an upper or lower predetermined set value limit at step S13. If it is beyond (Y), the indicating means indicates an alarm display 2 at step 514.

If there is no variation in vital signs (N) at step 58, the judging means 103 judges whether or not the value of vital sign is normal at step S15. If the value is normal (Y), the indicating means 104 erases all the alarm display and message display at step S16.

The above operations in sequence are repeated at predetermined intervals.

Figure 4:
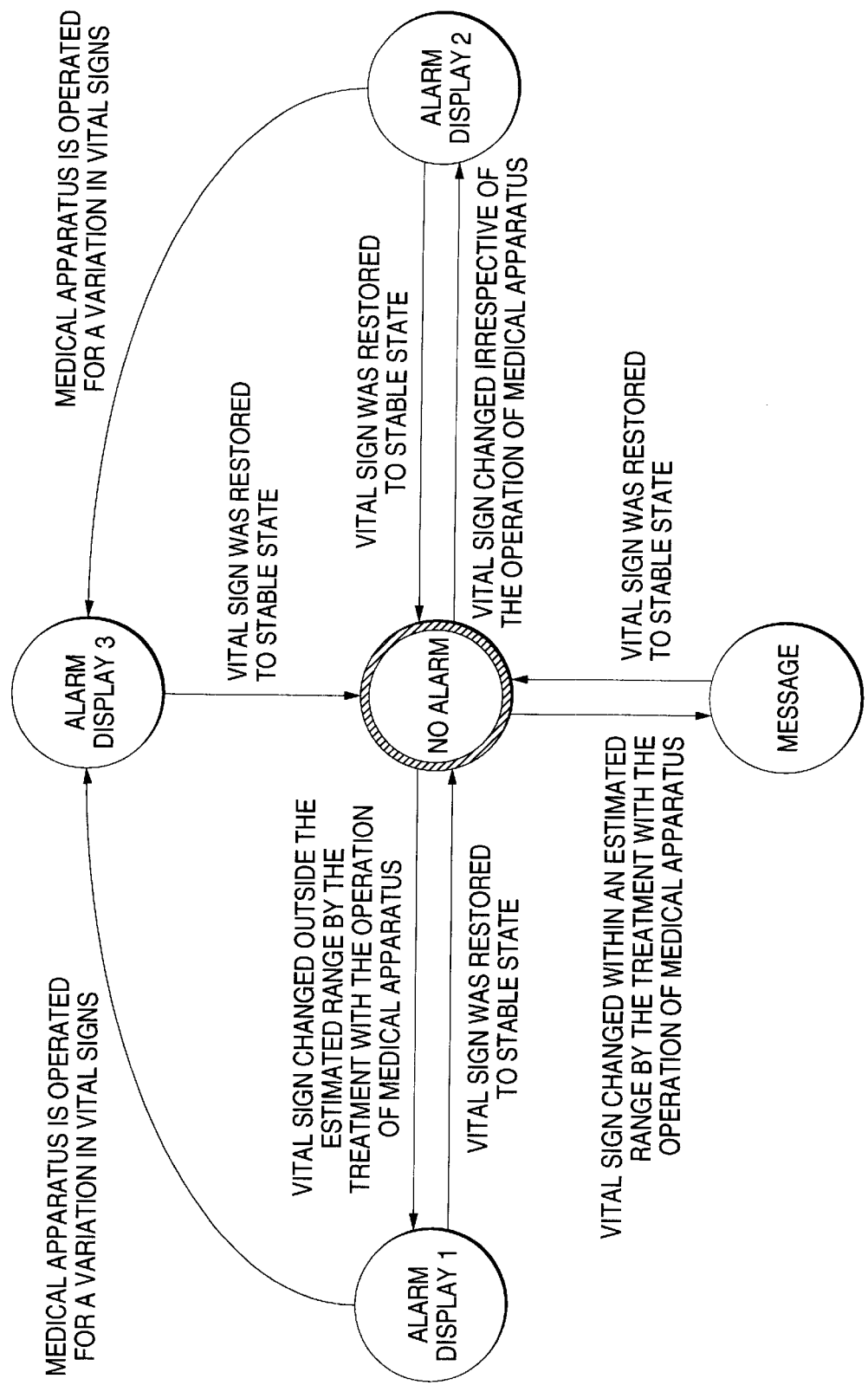
FIG. 4 is a state transition diagram showing the state transition between each alarm display and message in the vital sign monitor according to the embodiment of the invention.

FIG. 4 shows the state transition between each alarm display and the message in the operation of the vital sign monitor according to this embodiment of the invention.

Table 1 lists the specific phenomenal examples for determining the kind of display among the alarm displays and the message.

A table 2 as below lists the examples of output form of message and alarm displays in the indicating means.

TABLE 1

| State | condition | Example of Phenomenon | |
|---|---|---|---|
| Message | Variation in vital signs within estimated range by medical apparatus operation | ① | Normally estimated variation in vital signs owing to bronchial suction |
| | | ② | Normally estimated variation in vital signs owing to medication |
| Alarm display 1 | Sudden variation in vital signs by medical apparatus operation | ① | Excessive variation in vital signs owing to medication |
| | | ② | Abnormal reaction in vital signs owing to false medication |
| | No estimated variation in vital signs irrespective of medical apparatus operation | ① | No intended variation in vital signs irrespective of medication |
| Alarm display 2 | Variation in vital signs irrespective of treatment of medical practitioner | ① | Worse patient condition |
| Alarn display 3 | Operation of medical apparatus corresponding to alarm | ① | Treatment practice is made for alarm display |
| | | ② | Clinical staff confirms alarm display (staff is confirmed with the operation information of medical apparatus |

TABLE 2

| | Indication means | | | | |
|---|---|---|---|---|---|
| | | | speaker | | |
| Sort of Indication | Monitor display | Alarm sound | Sound indicating degree of variation | Alarm display (alarm pole) | Pager |
| Message | ○ *1 | — | ○ *2 | — | — |
| Alarm display 1 | ○ | ○ | Δ *2 | ○ | Δ *3 |

TABLE 2-continued

| | Indication means | | | | |
|---|---|---|---|---|---|
| | | speaker | | | |
| Sort of Indication | Monitor display | Alarm sound | Sound indicating degree of variation | Alarm display (alarm pole) | Pager |
| Alarm display 2 | ○ | ○ | Δ *2 | ○ | ○ |
| Alarm display 3 | ○ *4 | Δ *5 | ○ *2 | — | — |

*1: Display variation in vital signs by operation of medical apparatus.
*2: Change step of synchronizing tone for heart rate. However, alarm sound is preferential, if indicated.
*3: Notify only alarm needed for taking urgent treatment
*4: Indicate necessary treatment has been made for alarm display
*5: Adjust alarm sound corresponding to situation

EXAMPLES

Examples 1 to 3 appearing remarkable effect of the vital sign monitor of this embodiment will be described below in detail.

Example 1

The Vital Sign is the Blood Pressure, and the Medical Apparatus is an Infusion Pump FIGS. 5(a) to (f) shows an example 1 appearing the remarkable effect of the vital sign monitor of this embodiment.

Figure 5:
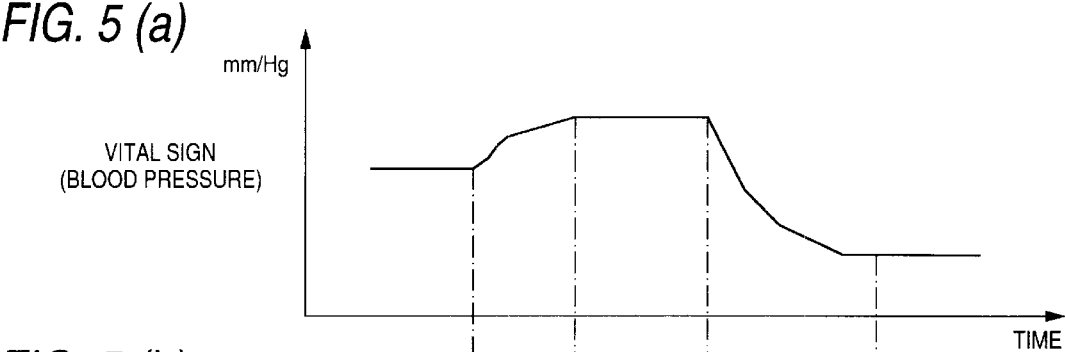
FIGS. 5(a) to (f) are diagrams for explaining an example 1 appearing the effect of the vital sign monitor according to the embodiment of the invention excellently.
Figure 5:
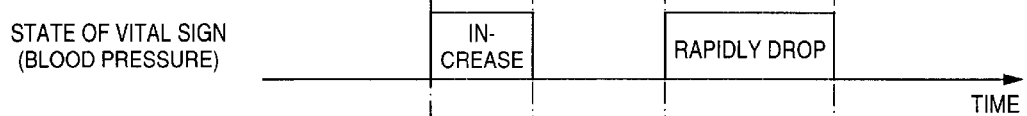
Figure 5:
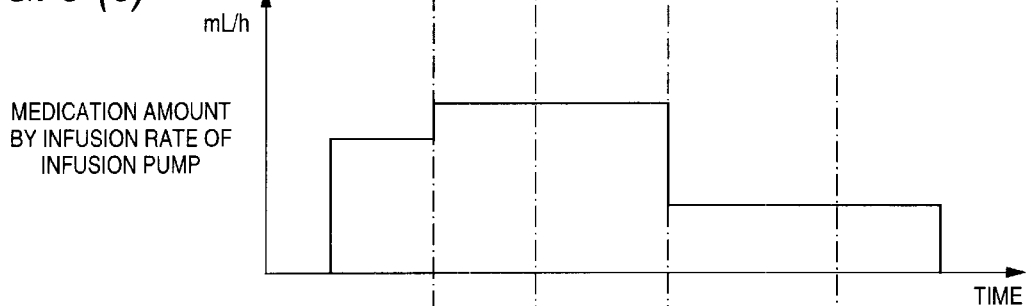
Figure 5:
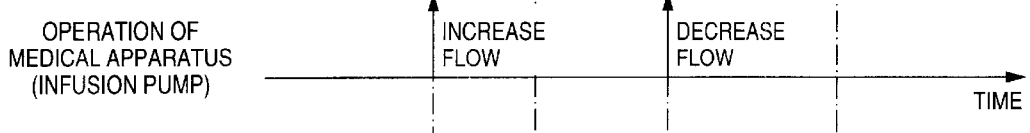
Figure 5:
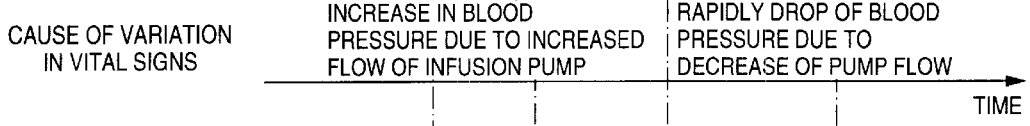
Figure 5:
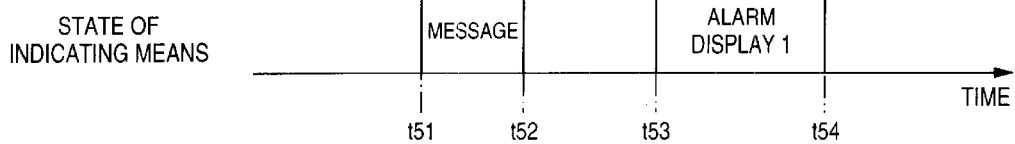
Figure 8:
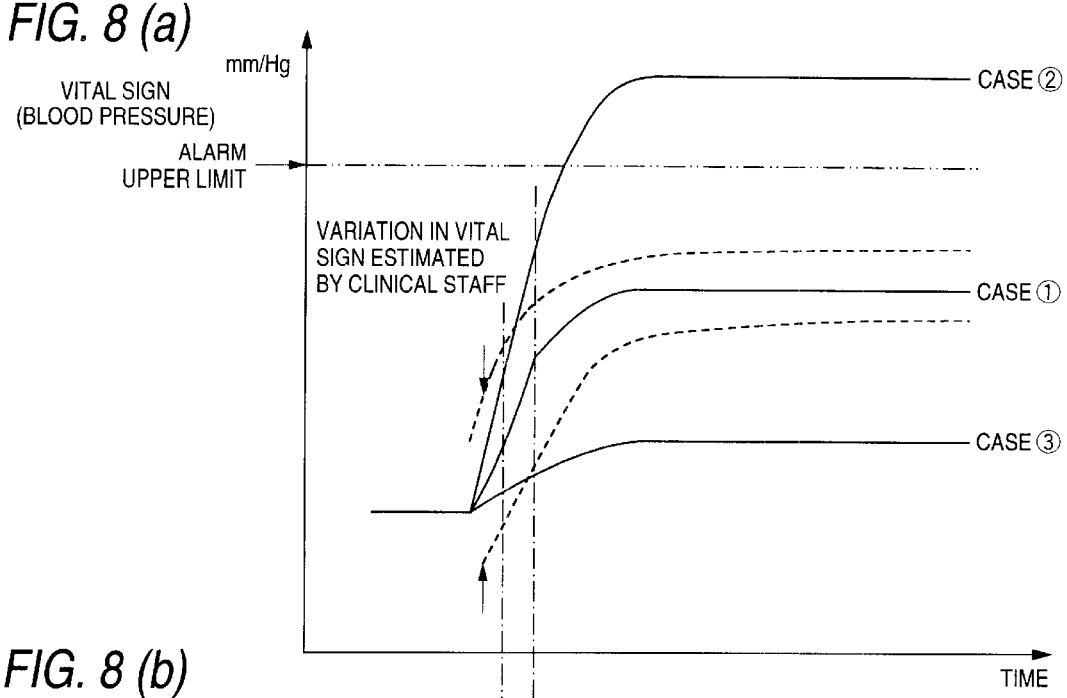
FIGS. 8(a) to (e) are diagrams for explaining the criterion of whether or not there is an estimated variation in vital signs when the medical apparatus is operated.
Figure 8:
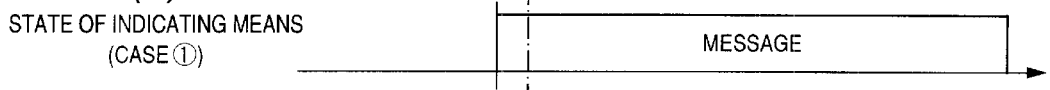
Figure 8:
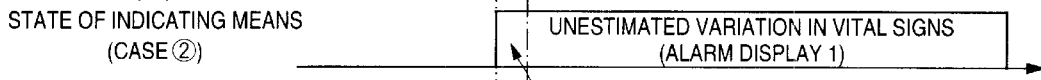
Figure 8:
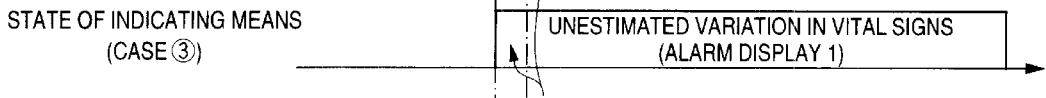
Figure 8:
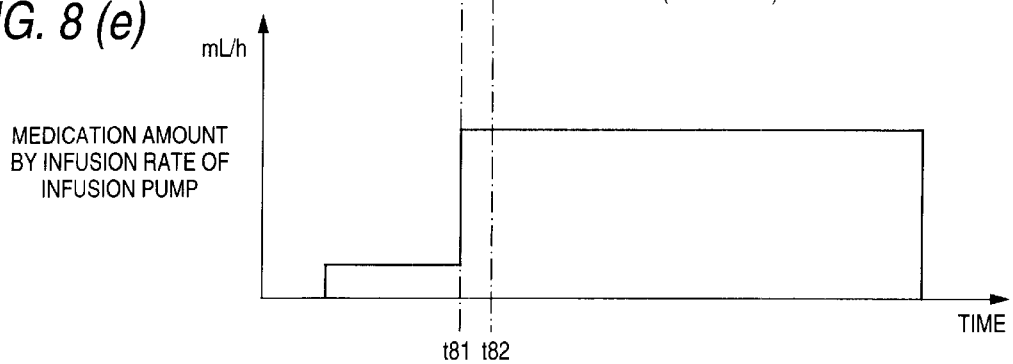

As shown in FIG. 5, at time t51, the amount of medication by infusion rate of an infusion pump to the patient was increased, so that the blood pressure was raised, and then stable at a constant value for a fixed time. At time t53, the flow of infusion pump was decreased, so that the blood pressure suddenly dropped (step S1: detect the vital signs, step S2: recognize the variation in vital signs, step S3: detect the practice of clinical staff, step S4: recognize the practice of clinical staff).

The operation of the vital sign monitor in this example will be described below.

At time t51, the judgement of step S8 (variation in vital signs) was "Y", and the judgement of step S9 (operation of medical apparatus) was also "Y". Moreover, at step S10 (estimated variation in vital signs), the judgement was "Y", because the increase in blood pressure due to an increased flow of infusion pump was within the estimated range. As a result, step S11 (message display) was made.

At time t52, the judgement of step S8 (variation in vital signs) was "N". At step 515 (normal vital sign), the judgement was "Y", because the blood pressure value was in the normal state. As a result, step S16 (erase the alarm and message display) was performed.

At time t53, the judgement of step S8 (variation in vital signs) was "Y", and the judgement of step S9 (operation of medical apparatus) was also "Y". Moreover, at step S10 (estimated variation in vital signs), the judgement was "N", because the blood pressure suddenly dropped due to a decreased flow of infusion pump. As a result, step S12 (alarm 1) was made.

At time t54, the judgement of step S8 (variation in vital signs) was "N". At step S15 (normal vital sign), the judgement was "Y", because the blood pressure was in the normal state. As a result, step S16 (erase alarm and message display) was performed.

Since the vital sign monitor is operated as described above, the clinical staff can be informed that "the variation in vital signs is within the estimated range by the operation of medical apparatus" as listed in Table 1 with the "message display" at time t51, and that "the variation in vital signs has suddenly occurred by the operation of medical apparatus" with the "alarm 1" at time t53.

Further, the patient is recovered to the normal condition to erase the alarm display 1 at time t54. Therefore, other patients are not obstructed from sleeping.

Example 2

The Vital Sign is the Blood Pressure and the Medical Apparatus is an Infusion Pump FIG. 6(a) to (f) are diagrams for explaining an example 2 appearing the remarkable effect of the vital sign monitor of this embodiment.

As shown in FIGS. 6(a) to (f), at time t61, the condition of the patient became worseand blood pressure drops, and lapsed into a (dangerous) state of low blood pressure. At time t62, the medication (treatment) through the infusion pump was made, so that the blood pressure was increased (recovered). At time t63, the blood pressure was kept constant (step S1: detect the vital signs, step S2: recognize the variation in vital signs, step S3: detect the practice of clinical staff, step S4: recognize the practice of clinical staff).

The operation of the vital sign monitor in this example will be described below.

At time t61, the judgement of step S8 (variation in vital signs) was "Y", and the judgement of step S9 (operation of medical apparatus) was "N". At step S13 (whether the upper or lower set value limit was exceeded), the judgement was "Y", because the variation of blood pressure exceeded the fluctuation range under the stable patient's condition. As a result, step S14 (alarm 2) was performed.

At time t62, the judgement of step S5 (whether the alarm 1 or 2 is indicated) was "Y", and the judgement of step S6 (the operation of medical apparatus corresponding to the alarm) was "Y". As a result, step S7 (alarm 3) was performed.

At time t63, the judgement of step S8 (variation in vital signs) was "N", and the judgement of step S15 (normal vital sign) was "Y", because the blood pressure was in the normal state. As a result, step S16 (erase the alarm and message display) was performed.

Since the vital sign monitor is operated as described above, the clinical staff can be informed that "the variation in vital signs has occurred irrespective of the treatment of the clinical staff" as listed in Table 1 with the "alarm 2" at time t61, and that "the medical apparatus corresponding to the announced alarm has operated" with the "alarm 3" because the clinical staff has made some treatment at time t62.

Further, the patient is recovered to the normal condition to erase the alarm 3 at time t63. Therefore, other patients are not obstructed from sleeping.

Example 3

The Vital Signs are Heart Rate and Respiration Rate, and the Medical Apparatus is an Ventilator FIGS. 7(a) to (g) are diagrams for explaining an example 3 appearing the remarkable effect of the vital sign monitor of this embodiment.

In this example 3, the patient has showed the normal reaction in making a bronchial suction through the ventilator.

As shown in FIGS. 7(a) to (g), at time t71, the medical apparatus regarding the bronchial suction was operated through the ventilator, so that the heart rate and the respiration rate of the patient increased. At time t72, the heart rate and the respiration rate of the patient stopped to increase, and began to decrease. At time t73, the heart rate and the respiration rate of the patient stopped to decrease, and was kept constant (at a value before the bronchial suction) (step S1: detect the vital signs, step S2: recognize the variation in vital signs, step S3: detect the practice of clinical staff, step S4: recognize the practice of clinical staff).

The operation of the vital sign monitor in this example will be described below.

At time t71, the judgement of step S8 (variation in vital signs) was "Y", and the judgement of step S9 (operation of medical apparatus) was "Y". Further, at step S10 (estimated variation in vital signs), the judgement was "Y", because the variation in the heart rate and respiration rate of the patient due to the operation of the ventilator was within the estimated range). As a result, step S11 (message display) was performed.

At time t73, the judgement of step S8 (variation in vital signs) was "N", and the judgement of step S15 (normal vital signs) was "Y", because the heart rate and respiration rate of the patient was in the normal state. As a result, step S16 (erase alarm and message display) was performed.

Since the vital sign monitor is operated as described above, the clinical staff can be informed that "the variation in vital signs has occurred within the estimated range by the operation of the medical apparatus" as listed in Table 1 with the "message display" at time t71.

Further, the patient is recovered to the normal condition to erase the message display at time t73. Therefore, other patients are not obstructed from sleeping.

In the above explanation, a criterion as to whether or not there is any estimated variation in vital signs by operating the medical apparatus will be described below in detail with reference to FIGS. 8(a) to (e).

In FIGS. 8(a) to (e), when the amount of medication by infusion rate of the infusion pump is increased, the variation in the blood pressure value of the patient occurs in a case ① of normal variation, a case ② beyond the range of variation estimated by the clinical staff, and a case ③ below that range.

AT time t81, the amount of medication by infusion rate of the infusion pump is increased, so that the blood pressure value is higher in the case ①, case ② and case ③. In all these cases, the blood pressure is within the range of variation estimated by the clinical staff (denoted by the dotted line), with no alarm indicated.

The case ① is within the estimated variation range so that the message is indicated at time 82. Next, at time t82, in the case ②, the blood pressure is beyond the estimated variation range (denoted by the dotted line) by the clinical staff, and in the case ③, the blood pressure is below that range. Therefore, in the cases ② and ③, the alarm 1 is indicated from time t82.

The unestimated variation in vital signs may possibly occur between time t81 and time t82, but no alarm is indicated yet.

On the contrary, in the case ① from time t82 on, the blood pressure value is within the estimated range of variation by the clinical staff, and no alarm is indicated.

As above described, the criterion was the estimated range of variation by the clinical staff as denoted by the dotted line. However, another criterion may be employed in which the alarm is indicated if a certain value is exceeded (as denoted by the chain line in the figure). The criterion may be appropriately defined, depending on the sort of vital sign and the type of medical apparatus.

As described above in detail, in the first aspect of the present invention, a vital sign monitor is provided by comprising vital sign detecting means for detecting vital signs, medical apparatus operation detecting means for detecting the operation of a medical apparatus, and judging means for judging the correlation between the vital signs and a medical apparatus operation condition on the basis of the vital signs detected by the vital sign detecting means and the operation condition of the medical apparatus detected by the medical apparatus operation detecting means. Therefore, the cause of a variation in vital signs can be recognized, and the unestimated variation in vital signs can be discriminated to suppress unnecessary alarm indication.

According to the second aspect of the present invention, the vital sign monitor is provided by further comprising indicating means for indicating the correlation between the vital signs and the medical apparatus operation condition as an alarm or a message depending upon an instruction signal of the judging means. Therefore, the alarm or message can be indicated in view of the presence or absence of the operation of the medical apparatus.

According to the third aspect of the present invention, the vital sign monitor includes the judging means which judges whether or not a variation in the vital signs detected by the vital sign detecting means is within a range of variation estimated from the operation of the medical apparatus detected by the medical apparatus operation detecting means. Hence, it is possible to make sure of whether or not the variation in vital signs is within the estimated range of variation.

According to the fourth aspect of the present invention, the vital sign monitor includes the indicating means indicates an alarm or a message on the basis of a judgement result of whether or not the variation in vital signs is within the range of variation estimated. It is possible to make sure of whether or not the variation in vital signs is within the estimated range of variation in terms of an alarm or a message.

According to the fifth aspect of the present invention, the vital sign monitor includes the judging means further judges whether or not the variation in the vital signs detected by the vital sign detecting means is beyond a predetermined range in a state where any change in the operation condition of the medical apparatus is not detected by the medical apparatus operation detecting means, and the indicating means indicates with an alarm that the predetermined range is exceeded. Hence, it is possible to make sure of the variation in vital signs irrespective of the operation of the medical apparatus.

According to the sixth aspect of the present invention, in the vital sign monitor, in the case where the indicating means indicates the alarm in accordance with the correlation when the operation condition of the medical apparatus is detected by the medical apparatus operation detecting means, the judging means instructs the indicating means to indicate by an alarm a state of the operation condition of the medical apparatus.

According to the seventh aspect of the present invention, in the vital sign monitor, the vital sign detecting means for detecting vital signs, clinical staff practice recognizing means for detecting and recognizing a practice of a clinical staff, and judging means for judging the correlation between the vital signs and the practice of the clinical staff on the basis of the vital signs detected by the vital sign detecting means and the practice of the clinical staff recognized by the clinical staff practice recognizing means. Hence, the cause of a variation in vital signs can be recognized.

According to eighth aspect of the present invention, in the vital sign monitor, the indicating means for indicating the correlation between the vital signs and the practice of the clinical staff as an alarm or a message depending upon an instruction signal of the judging means. Hence, the alarm or message can be indicated in consideration of the practice of the clinical staff.

According to the ninth aspect of the present invention, in the vital sign monitor, the judging means judges whether or not a variation in the vital signs detected by the vital sign detecting means is within a range of variation estimated from the practice of the clinical staff recognized by the clinical staff practice recognizing means. Hence, it is possible to make sure of whether or not the variation in vital signs is within the estimated range of variation.

According to the tenth aspect of the present invention, in the vital sign monitor, the indicating means indicates an alarm or a message on the basis of a judgement result of whether or not the variation in the vital signs is within the estimated range of variation. Hence, it is possible to make sure of whether or not the variation in vital signs is within the estimated range of variation in terms of an alarm or a message.

According to the eleventh aspect of the present invention, in the vital sign monitor, the judging means further judges whether or not a variation in the vital signs detected by the vital sign detecting means is beyond a predetermined range in the state where no change in the practice of the clinical staff is detected by the clinical staff practice recognizing means, and the indicating means indicates with an alarm that the predetermined range is exceeded. Hence, it is possible to make sure of the variation in vital signs irrespective of the practice of the clinical staff.

According to the twelfth aspect of the present invention, in the vital sign monitor, in the case where the indicating means indicates the alarm in accordance with the correlation when the operation condition of the medical apparatus is detected by the medical apparatus operation detecting means, the judging means instructs the indicating means to indicate by an alarm a state of the operation condition of the medical apparatus.

According to the thirteenth aspect of the present invention, in the vital sign monitor, the clinical staff practice recognizing means recognizes the practice of the clinical staff when the medical apparatus is operated.

According to the fourteenth aspect of the present invention, in the vital sign monitor, the clinical staff practice recognizing means recognizes the practice of the clinical staff using image-pickup means.

According to the fifteenth aspect of the present invention, in the vital sign monitor using the image-pickup means, it is recognized that the clinical staff changes the body position of a patient, or there is a body movement of the patient, the indicating means is inhibited to indicate the alarm. Hence, it is possible to suppress unnecessary alarm for the practice of the treatment care by the clinical staff or the body movement of the patient.

With the vital sign monitor of the invention as described above, the cause of the variation in vital signs can be recognized in consideration of the medical practice of the clinical staff, thereby suppressing unnecessary alarm display for the clinical staff, and discriminating the variation in vital signs that is not estimated by the clinical staff. Hence, a highly reliable alarm function can be implemented.

Moreover, the vital sign monitor can be implemented with a function of suppressing the alarm display on the basis of an operation of the medical apparatus with the alarm. Hence, unnecessary operation for the clinical staff can be dispensed with. The clinical staff can be intent on the treatment practice, and does not directly touch on the vital sign monitor, resulting in less danger of hospital acquired infection.

What is claimed is:

1. A vital sign monitor comprising:
   vital sign detecting means for detecting at least one kind of vital sign;
   medical apparatus operation detecting means for detecting the operation of a medical apparatus; and
   judging means for judging a correlation between the vital sign and a medical apparatus operation condition on the basis of said vital sign detected by the vital sign detecting means and the operation condition of the medical apparatus detected by the medical apparatus operation detecting means.

2. The vital sign monitor according to claim 1, further comprising:
   indicating means for indicating the correlation between the vital sign and the medical apparatus operation condition as an alarm or a message depending upon an instruction signal of the judging means.

3. The vital sign monitor according to claim 2, wherein the judging means further judges whether or not a variation in said vital sign detected by said vital sign detecting means is beyond a predetermined range in a state where any change in the operation condition of said medical apparatus is not detected by said medical apparatus operation detecting means, and said indicating means indicates an alarm indicating that said predetermined range is exceeded.

4. The vital sign monitor according to claim 2, wherein in the case where the indicating means indicates the alarm in accordance with the correlation when the operation condition of the medical apparatus is detected by the medical apparatus operation detecting means, the judging means instructs the indicating means to indicate an alarm indicating a state of the operation condition of the medical apparatus.

5. The vital sign monitor according to claim 1, wherein the judging means judges whether or not a variation in the vital sign detected by said vital sign detecting means is within a range of variation estimated from the operation of said medical apparatus detected by said medical apparatus operation detecting means.

6. The vital sign monitor according to claim 5, further comprising:
   an indicating means for indicating the correlation between the vital sign and the medical apparatus operation condition as an alarm or a message depending upon an instruction signal of the judging means,
   wherein the indicating means indicates at least one of an alarm and a message on the basis of a judgement result whether or not the variation in said vital sign is within the range of variation estimated.

7. The vital sign monitor according to claim 1, wherein the medical apparatus is a ventilator.

8. The vital sign monitor according to claim 1, wherein the medical apparatus is an infusion pump.

9. A vital sign monitor comprising:
   vital sign detecting means for detecting at least one kind of vital sign;
   medical apparatus operation detecting means for detecting an operation of a medical apparatus;
   judging means for judging whether a variation in the vital sign is within a range of variation estimated from the operation of the medical apparatus, and issuing an instruction signal depending on the judgement;
   first indicating means for indicating a first alarm based on the instruction signal; and
   second indicating means for indicating a second alarm based on the operation of the medical apparatus after the first alarm is indicated.

10. A vital sign monitor comprising:
    vital sign detecting means for detecting at least one kind of vital sign;
    medical apparatus operation detecting means for detecting an operation of a medical apparatus;
    judging means for judging whether the vital sign varies irrespective of the operation of the medical apparatus, and issuing an instruction signal depending on the judgement;
    first indicating means for indicating a first alarm based on the instruction signal; and
    second indicating means for indicating a second alarm based on the operation of the medical apparatus after the first alarm is indicated.

* * * * *